(12) United States Patent
Germanson et al.

(10) Patent No.: US 9,539,428 B2
(45) Date of Patent: Jan. 10, 2017

(54) ISOLATING LEAD CONDUCTOR FOR FAULT DETECTION

(75) Inventors: Nancy M. Germanson, Maple Grove, MN (US); Thomas H. Spear, Bloomington, MN (US); Patrick David Miller, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 1469 days.

(21) Appl. No.: 13/014,965

(22) Filed: Jan. 27, 2011

(65) Prior Publication Data

US 2012/0197331 A1    Aug. 2, 2012

(51) Int. Cl.
| | | |
|---|---|---|
| *A61N 1/37* | (2006.01) | |
| *A61B 6/00* | (2006.01) | |
| *A61N 1/39* | (2006.01) | |
| *A61N 1/08* | (2006.01) | |
| *G01R 31/02* | (2006.01) | |

(52) U.S. Cl.
CPC ........... *A61N 1/3706* (2013.01); *A61N 1/3925* (2013.01); *A61N 2001/083* (2013.01); *G01R 31/024* (2013.01)

(58) Field of Classification Search
CPC  A61N 2001/083; A61N 1/3706; A61N 1/025; A61N 1/372; A61N 1/3925; A61B 6/586
USPC ............................................. 607/37, 38, 148
See application file for complete search history.

(56) References Cited

U.S. PATENT DOCUMENTS

| | | |
|---|---|---|
| 3,888,261 A | 6/1975 | Maurer |
| 4,105,900 A | 8/1978 | Martin et al. |
| 4,140,131 A | 2/1979 | Dutcher et al. |
| 4,549,548 A | 10/1985 | Wittkampf et al. |
| 4,579,119 A | 4/1986 | Callaghan |

(Continued)

FOREIGN PATENT DOCUMENTS

| | | |
|---|---|---|
| EP | 0715866 A2 | 6/1996 |
| WO | 98/42406 A1 | 10/1998 |

(Continued)

OTHER PUBLICATIONS

Case Report, "Early Detection of Lead Fracture by Painless High Voltage Lead Impedance Measurement in a Transvenous ICD Lead System", by Jens Stevens MD., et al., Journal of Interventional Cardiac Electrophysiology 4, 269-272 (2000).

(Continued)

*Primary Examiner* — Christopher D Koharski
*Assistant Examiner* — Natasha Patel
(74) *Attorney, Agent, or Firm* — Evans M. Mburu

(57) ABSTRACT

Systems and methods for providing a cardiac stimulus device lead having fault tolerance and fault isolation are disclosed. A medical electrical lead is provided according to one aspect. According to one embodiment, the lead includes a first conductor and a second conductor for transmitting an electrical pulse from a pulse generator. The lead further includes a switching mechanism, a first electrode, and a lead assessment circuit. The switching mechanism selectively couples the first conductor to the first electrode. The first electrode is decoupled during a test phase and the switching mechanism directly couples the first conductor to the second conductor. The lead assessment circuit processes a signal associated with the electrical properties of the lead to determine whether the lead is exhibiting a lead related condition.

15 Claims, 8 Drawing Sheets

(56) References Cited

U.S. PATENT DOCUMENTS

| | | | |
|---|---|---|---|
| 4,606,349 A | 8/1986 | Livingston et al. |
| 4,620,303 A | 10/1986 | Tschoepe |
| 4,899,750 A | 2/1990 | Ekwall |
| 4,916,612 A | 4/1990 | Chin et al. |
| 5,003,975 A | 4/1991 | Hafelfinger et al. |
| 5,117,824 A | 6/1992 | Keimel et al. |
| 5,137,021 A | 8/1992 | Wayne et al. |
| 5,156,149 A | 10/1992 | Hudrlik |
| 5,184,614 A | 2/1993 | Collins et al. |
| 5,201,808 A | 4/1993 | Steinhaus et al. |
| 5,201,865 A | 4/1993 | Kuehn |
| 5,224,475 A | 7/1993 | Berg et al. |
| 5,344,430 A | 9/1994 | Berg et al. |
| 5,350,410 A | 9/1994 | Kleks et al. |
| 5,361,776 A | 11/1994 | Samuelson et al. |
| 5,402,070 A | 3/1995 | Shelton et al. |
| 5,431,692 A | 7/1995 | Hansen et al. |
| 5,453,468 A | 9/1995 | Mascia et al. |
| 5,476,485 A | 12/1995 | Weinberg et al. |
| 5,507,786 A | 4/1996 | Morgan et al. |
| 5,534,018 A | 7/1996 | Wahlstrand et al. |
| 5,549,646 A | 8/1996 | Katz et al. |
| 5,571,156 A * | 11/1996 | Schmukler | 607/116 |
| 5,722,997 A | 3/1998 | Nedungadi et al. |
| 5,741,311 A | 4/1998 | Mc Venes et al. |
| 5,755,742 A | 5/1998 | Schuelke et al. |
| 5,765,031 A | 6/1998 | Mimuth et al. |
| 5,814,088 A | 9/1998 | Paul et al. |
| 5,891,179 A | 4/1999 | Er et al. |
| 5,944,746 A | 8/1999 | Kroll |
| 6,052,753 A | 4/2000 | Doerenberg et al. |
| 6,445,951 B1 | 9/2002 | Mouchawar |
| 6,493,586 B1 | 12/2002 | Stahmann et al. |
| 6,721,600 B2 | 4/2004 | Jorgenson et al. |
| 6,859,667 B2 | 2/2005 | Goode |
| 6,871,091 B2 | 3/2005 | Wilkinson et al. |
| 7,047,083 B2 | 5/2006 | Gunderson et al. |
| 7,149,580 B2 | 12/2006 | Conley et al. |
| 7,225,025 B2 | 5/2007 | Goode |
| 7,236,834 B2 | 6/2007 | Christopherson et al. |
| 7,389,144 B1 | 6/2008 | Osorio et al. |
| 7,515,961 B2 | 4/2009 | Germanson et al. |
| 2002/0120307 A1 | 8/2002 | Jorgenson et al. |
| 2003/0204233 A1 | 10/2003 | Laske et al. |
| 2004/0059396 A1 * | 3/2004 | Reinke et al. | 607/60 |
| 2005/0043768 A1 | 2/2005 | Goode |
| 2005/0090870 A1 | 4/2005 | Hine et al. |
| 2006/0064149 A1 | 3/2006 | Belacazar et al. |
| 2007/0265674 A1 | 11/2007 | Olson et al. |
| 2010/0027176 A1 | 2/2010 | Kawate et al. |
| 2010/0063561 A1 * | 3/2010 | Sloman et al. | 607/27 |
| 2010/0106206 A1 | 4/2010 | Aghassian et al. |
| 2010/0114222 A1 | 5/2010 | Gunderson et al. |
| 2010/0217366 A1 | 8/2010 | Moulder et al. |
| 2010/0324640 A1 | 12/2010 | Bauer et al. |
| 2011/0054554 A1 | 3/2011 | Swerdlow |

FOREIGN PATENT DOCUMENTS

| | | |
|---|---|---|
| WO | 2009082783 | 7/2009 |
| WO | 2010/008833 A1 | 1/2010 |
| WO | 2010056501 A1 | 5/2010 |

OTHER PUBLICATIONS

NASA Office of Logic Design, "Fault Tolerant Design", Preferred Reliability Practices No. PD-ED-1246, Sep. 21, 1995, pp. 1-4.

Avizienis et al., "Basic Concepts and Taxonomy of Dependable and Secure Computing", IEEE Transactions on Dependable and Secure Computing, vol. 1, No. 1, Jan.-Mar. 2004, pp. 11-33.

Avizienis, "Toward Systematic Design of Fault-Tolerant Systems", IEEE, Apr. 1997, pp. 51-58.

Dorwarth et al., "Transvenous Defibrillation Leads: High Incidence of Failure During Long-Term Follow-Up", J. Cardiovascular Electrophysiol., vol. 14, Jan. 2003, pp. 38-43.

(PCT/US2012/021155) PCT Notification of Transmittal of the International Search Report and the Written Opinion of the International Searching Authority, Mailed May 10, 2012, 9 pages.

* cited by examiner

ISOLATING LEAD CONDUCTOR FOR FAULT DETECTION

CROSS-REFERENCE TO RELATED APPLICATION

Cross-reference is hereby made to the commonly-assigned related U.S. patent application Ser. No. 13/015,042 (now issued as U.S. Pat. No. 8,463,384), filed on even date herewith entitled "ISOLATED LEAD CONDUCTOR MEASUREMENTS FOR FAULT DETECTION" (P0033896.01) incorporated herein by reference in its entirety.

FIELD

The present disclosure relates to implantable medical devices. More particularly, this disclosure pertains to medical electrical lead systems for detecting and isolating lead-related conditions.

BACKGROUND

A wide variety of implanted medical devices (IMDs) for delivering a therapy or monitoring a physiologic condition which can employ one or more elongated electrical leads and/or sensors are available. Such IMDs can monitor or deliver therapy to the heart, muscle, nerve, brain, and stomach or other organs. Examples of such IMDs include implantable cardioverter defibrillator devices, which have a pulse generator and one or more electrical leads with one or more electrodes that conduct signals to and receive signals from the patient's heart.

These electrical lead(s) and their electrode(s) are placed in or proximate to the organ such that an electrical signal between electrodes is capable of stimulating the organ. The electrodes may be configured either to deliver a stimulus to the organ, or to detect or sense an intrinsic electrical event associated with the organ. A programming device or programmer communicates with the medical device through a communication link. One example of a communication link is a telemetry link that provides means for commands and data to be non-invasively transmitted and received between the programmer and the device.

Leads associated with IMDs typically include a lead body extending between a proximal lead end and a distal lead end and incorporate one or more exposed electrode or sensor elements located at or near the distal lead end. One or more elongated electrical conductors extend through the lead body from a connector assembly provided at a proximal lead end for connection with an associated IMD to an electrode located at the distal lead end or along a section of the lead body. Each electrical conductor is typically electrically isolated from any other electrical conductors and is encased within an outer sheath that electrically insulates the lead conductors from body tissue and fluids.

Implantable medical leads can extend from a subcutaneous implantation site of the IMD through an internal body pathway to a desired tissue site. The leads are generally preferred having small diameter, highly flexible, reliable lead bodies that withstand degradation by body fluids and body movements that apply stress and strain to the lead body and the connections made to electrodes. As lead bodies are made smaller and smaller and the number of lead conductors is increased or maintained, the integrity of lead conductors is increasingly important.

Continuous flexing of the cardiac lead bodies due to the beating of the heart, for example, is also an important consideration in maintaining the lead integrity. Other stresses are applied to the lead body during an implantation or lead repositioning procedure. Movements by the patient can cause the route traversed by the lead body to be constricted or otherwise altered causing stresses on the lead body. At times, the lead bodies can be slightly damaged during surgical implantation, and the slight damage can progress in the body environment until a lead conductor fractures and/or the insulation is breached. The effects of lead body damage can progress from an intermittent manifestation to a more continuous effect. In extreme cases, insulation of one or more of the electrical conductors can be breached, causing the conductors to contact one another or body fluids resulting in a low impedance or short circuit. In other cases, a lead conductor can fracture and exhibit an intermittent or continuous open circuit resulting in an intermittent or continuous high impedance.

Such lead issues resulting in short or open circuits, for example, can be referred to, for simplicity, as "lead-related conditions." In the case of cardiac leads, the ability to sense cardiac activity conditions accurately through a lead can be impaired by these lead-related conditions. Complete lead breakage impedes any sensing functions while lead conductor fractures or intermittent contact can demonstrate electrical noise that interferes with accurate sensing. During cardiac pacing or defibrillation, lead-related conditions can reduce the effectiveness of a pacing or defibrillation below that sufficient to pace or defibrillate the heart.

To detect these lead-related conditions, certain pacemakers and IMDs have been provided with the capability of storing cardiac electrogram data prompted by the automatic determination of oversensing or undersensing of cardiac events, loss of capture, out of range lead impedance measurements, etc. Such data is telemetered to an external instrument when the physician interrogates the IMD and used by the clinician to try to pinpoint a suspected lead-related condition. Another example for detecting a lead-related condition is based on lead impedance measurements. Such cardiac rhythm management systems have included circuitry that is capable of measuring the lead impedance (the impedance seen by the device across a pacing lead or sensing lead). Other solutions have included detecting a lead-related condition based on automatic detection of capture failure. One such method of detecting lead-related conditions has a dedicated unipolar evoked response channel with low capacitance that can detect the evoked response of the cardiac muscle activation following the pacing artifact. When the evoked response following the pacing pulse falls below an evoked response threshold, loss of capture is declared. A related example for detecting a lead-related condition is based on the pacing amplitude that is automatically adjusted by an autocapture system. If the pacing amplitude required to capture exceeds a threshold, the device may declare the existence of a lead-related condition.

However, the inventors of the present disclosure have determined that these conventional methods of evaluating the electrical properties of a lead to detect a lead-related condition are affected by the tissue of the organs in which the leads are implanted. Therefore, the present disclosure addresses the need in the art for a system and method for eliminating the measurement variations that are associated with the lead-to-tissue interface.

SUMMARY

One of the difficulties stemming from the conventional methods of evaluating the electrical properties of a medical electrical lead involves encapsulation, which is the process that occurs when a foreign body enters the human body. The encapsulation of an electrode, for example, is sometimes referred to as biofouling. The immune system of the human body recognizes the foreign body and tries to reject it by building a layer of tissue around the foreign body to protect the rest of the body. The inventors of the present disclosure have discovered that the precision and accuracy of the measurement of the electrical properties of the lead system can be improved by isolating the lead from the electrode to eliminate the variations that arise with fluctuations in tissue electrical properties over time.

In accordance with the foregoing, one embodiment includes a medical electrical lead with embedded intelligence to provide fault tolerance. The medical lead system is provided with a switching mechanism for electrically isolating the lead's distal end from tissue. In one example, the switching mechanism selectively couples and decouples an electrode to the distal end of a first conductor in the lead. The switching mechanism enables direct coupling of the first conductor to a second conductor disposed within the lead body when the electrode is decoupled from the lead.

In an embodiment, a medical electrical lead is provided with a first conductor being selectively coupled to a first electrode. A switching mechanism provides the selective coupling between the first conductor and the first electrode. A capacitor is disposed proximate to the distal end of the lead. The switching mechanism may be actuated to decouple the first electrode and directly couple the capacitor to a return path conductor or an alternative electrical node. The capacitor may then be charged and discharged through the first and second conductors with the discharge morphology being evaluated to diagnose lead-related conditions of the conductors.

In some implementations, a multiplex scheme is used to provide a time slot within a therapy delivery cycle for performing measurements of the lead electrical properties. Therefore, a pacing pulse may be transmitted through the conductors from a pulse generator to the lead electrodes in a first time slot, measurement of the lead electrical properties made in a second time slot, and intrinsic electrical cardiac signals transmitted over the conductors from the electrodes to the pulse generator in a third time slot. As such, the electrical properties of the lead may be measured without affecting the therapy delivery.

In another embodiment, a system for detecting lead-related conditions comprises an implantable medical device, a medical electrical lead subsystem, and a cardiac tissue subsystem. The cardiac tissue subsystem may be employed to isolate the lead subsystem from the tissue. A lead diagnostic unit comprising one or more modules may be implemented in the system for controlling the measurement of one or more electrical properties of the lead and evaluating the measured electrical properties to determine whether or not a lead-related condition is present.

In another embodiment, the system includes components to achieve functional reconfiguration on detection of a lead-related condition. Exemplary implementations may include switching means to redirect therapy delivery through alternate conductors in the lead.

In another example, a computer-readable medium includes instructions for causing a programmable processor to isolate a conductor within a lead from a tissue interface, deliver an electrical signal via an electrical path including at least the conductor, detect an electrical property of the conductor during the delivery of the electrical signal, and identify a lead-related condition when the detected delivered energy traverses a respective threshold.

Another aspect of the present disclosure is a method for delivering therapy to a patient with conductors of a medical lead and selectively isolating the conductors from the patient's tissue to perform a measurement of the electrical properties of the conductors. According to one embodiment of this method, a pulse may be generated by a pulse generator and transmitted through the isolated lead conductors. An electrical property of the lead conductors may be measured to determine whether a lead-related condition exists.

The foregoing summary information is intended to merely illustrate some of the aspects and features of the present disclosure and is not meant to limit the scope in any way. In fact, upon review of the foregoing and the following described and depicted embodiments one of skill in the art will surely recognize insubstantial modifications or extensions of the disclosure each of which is expressly intended to be covered hereby.

BRIEF DESCRIPTION OF THE DRAWINGS

Various aspects and features of the present disclosure will be readily appreciated as the same becomes better understood by reference to the detailed description when considered in connection with the accompanying drawings, in which like reference numerals designate like parts throughout the figures thereof and wherein.

DETAILED DESCRIPTION

The present disclosure provides diverse methods and apparatus for in vivo monitoring, detecting and/or predicting potential lead-related conditions or deleterious trends of chronically implanted medical electrical leads. Exemplary implementations will facilitate monitoring of the lead structure to enable detection of early indicators of lead degradation.

As used herein, lead-related condition generally refers to any condition prohibiting or frustrating use of the lead in the desired manner during normal operation of the cardiac rhythm management system. This includes but is not limited to parameters associated with physical conditions of the lead such as sensed noise, lead impedance outside a predetermined range, capture failure, capture amplitude voltage outside a predetermined range, intrinsic amplitude outside a predetermined range, failure to detect an expected event, and an electrical hardware failure.

Conventional electrical evaluations of medical leads in vivo have been based on impedance and threshold measurements. The traditional impedance measurements are based on output current and voltage measurements made in the implantable medical device while threshold measurements have been based on determination of the threshold pulse amplitude needed to achieve cardiac depolarization. However, the measurement pathways have included the lead conductor and the cardiac tissue interfacing with the electrodes. A conductive path including cardiac tissue causes variations in the electrical properties, such as impedance, of the conductive path that fluctuate over time because of changes in cardiac tissue properties and disease states. Also, variations in the electrical properties of a path including cardiac tissue may be affected by medication that the patient may have taken. These variations in the conductive path result in erratic electrical characteristics that make detection of transient and gradual changes in lead conductor impedances trending to the outer boundaries of specification ranges complicated and sometimes impossible.

The present disclosure provides for periodic measurements of lead conductor electrical properties to detect graduated conductor degradation trending without inclusion of cardiac tissue impedances. The ability to detect indicators trending toward potential lead degradation offers the opportunity to respond to medical lead stresses even before the graduated degradation process occurs thereby minimizing the impact of a lead-related condition to the patient.

Figure 1:
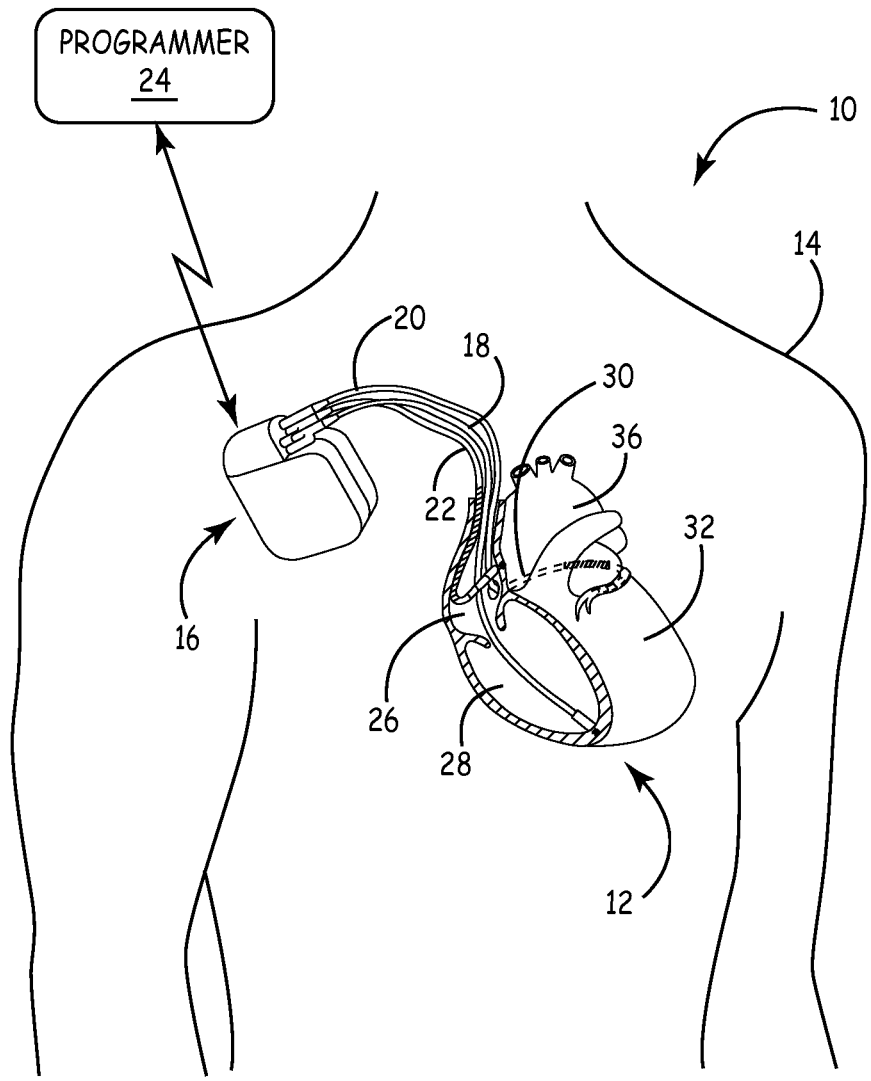
FIG. 1 is a conceptual drawing illustrating an example system that includes an implantable medical device (IMD) coupled to implantable medical leads.

FIG. 1 is a conceptual drawing illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

In the following examples, techniques are described for detecting lead-related conditions that may compromise the operation of a medical device, e.g., IMD 16. In the disclosed examples, a lead diagnostics unit of a device, e.g., IMD 16 identifies lead-related conditions by comparing one or more characteristics of the performance of leads 18, 20, and 22 during an evaluation phase to one or more predetermined criteria. In particular, the electrical characteristics of a lead conductor during the evaluation phase are monitored by the diagnostics unit and compared to the predetermined criteria, e.g., stored in a memory of IMD 16.

In the example of FIG. 1, leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. Exemplary configurations for electrodes used by IMD 16 for sensing and pacing may be unipolar, bipolar, quadrapolar or any other suitable vector(s). IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that receives input from a user. It should be noted that the user may also interact with programmer 24 via a patient monitor (not shown) and/or remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the performance or integrity of IMD 16 or other components of system 10, such as leads 18, 20 and 22, or a power source of IMD 16. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the rhythm of heart 12, trends therein over time, or arrhythmic episodes. In some examples, this information may be presented to the user as an alert. For example, a lead-related condition identified based on the delivered energy and/or lead impedance during a lead test may trigger IMD 16 to transmit an alert to the user via programmer 24.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
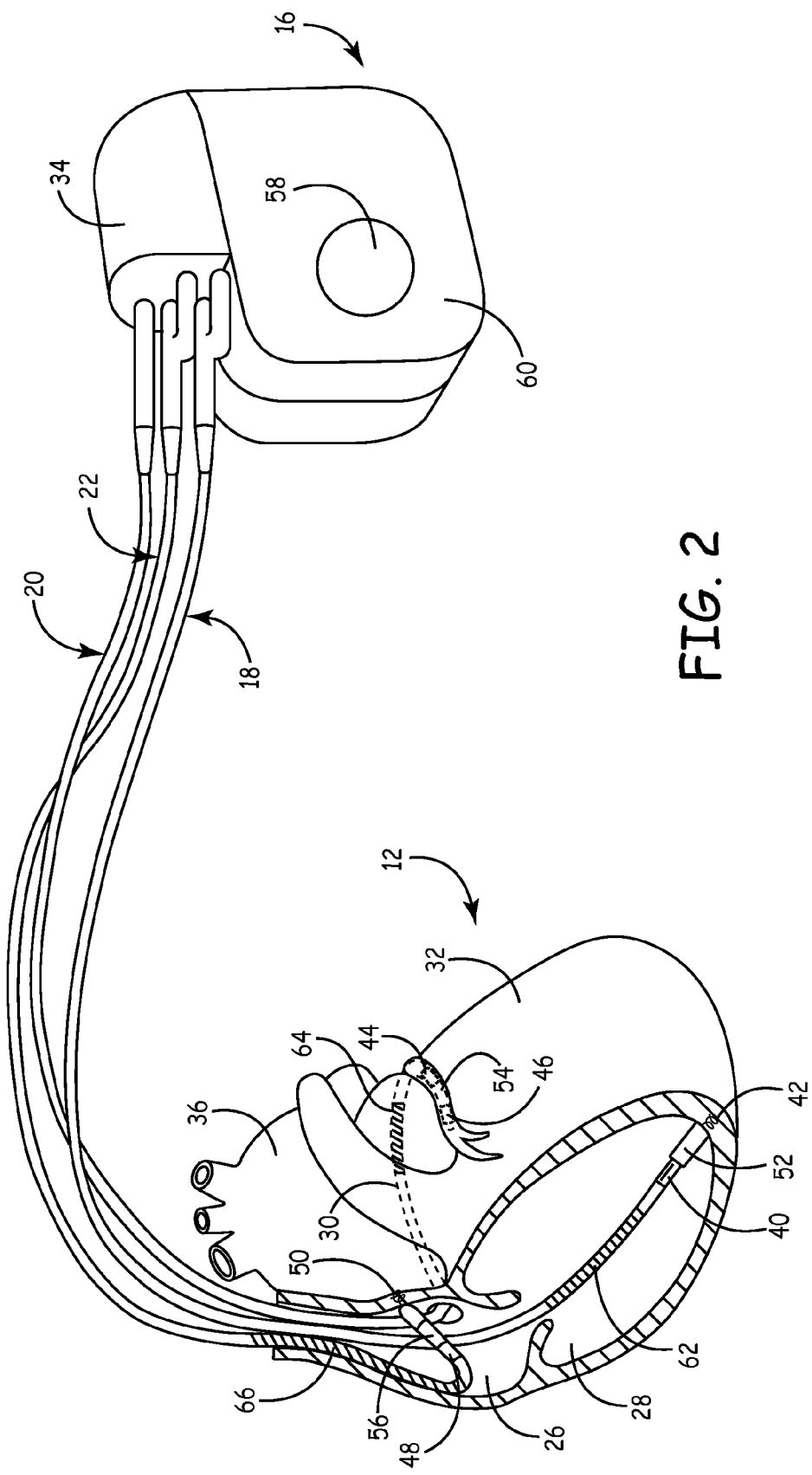
FIG. 2 is a conceptual drawing illustrating the example IMD and leads of FIG. in conjunction with a heart.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic electrical signals, test signals as well as a sensing module for monitoring the rhythm of heart 12. A test signal, as used herein, generally refers to electrical signals applied to conduct lead integrity assessment in accordance with principles of this disclosure.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
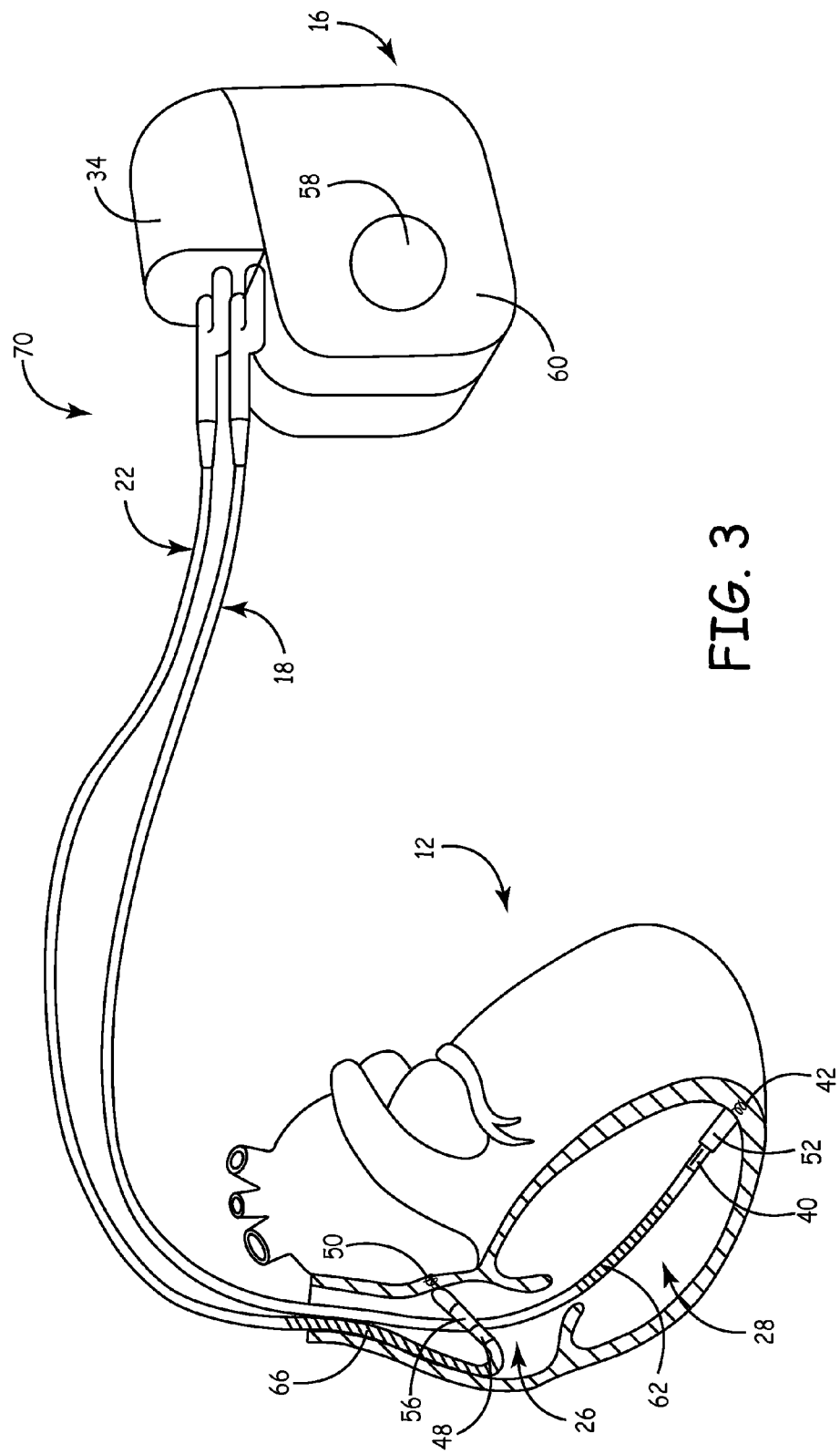
FIG. 3 is a conceptual drawing illustrating the example IMD of FIG. 1 coupled to a different configuration of implantable medical leads in conjunction with a heart.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing and/or stimulation configurations.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Detection of lead-related conditions according to this disclosure is applicable to lead systems having any specific number of leads.

Figure 4:
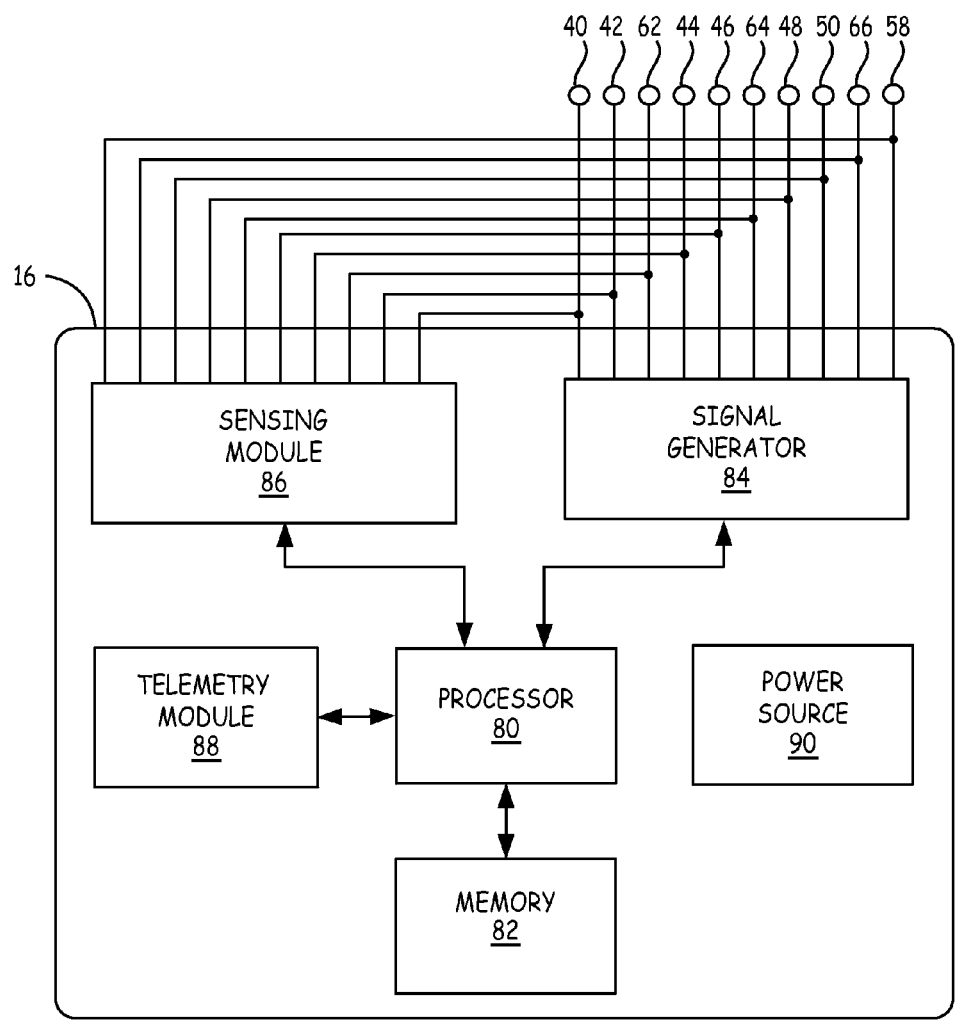
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to one or more selected therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 62, 64, and 66, e.g., via conductors of the respective lead 18, 20, 22 as will be discussed with reference to FIGS. 6 & 7. In the case of housing electrode 58 the coupling may be via an electrical conductor disposed within housing 60 of IMD 16. In the illustrated example, signal generator 84 is configured to generate and deliver signals for stimulation therapy and lead conductor testing. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers electrical energy for testing the lead conductors. The signal generator may deliver the signals in the form of pulses, sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, some various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the sensing electrodes that are selected for coupling to this wide-band amplifier may be converted to multi-bit digital signals by an analog-to-digital converter (ADC) provided by, for example, sensing module 86 or processor 80. In some examples, processor 80 may store the digitized versions of signals from the wide band channel in memory 82 as electrograms (EGMs). Processor 80 may employ digital signal analysis techniques to characterize the digitized signals from the wide band channel to, for example detect and classify the patient's heart rhythm. Processor 80 may detect and classify the patient's heart rhythm by employing any signal processing methodologies appropriate for the intended application or applications of IMD 16.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24.

In addition, processor 80 may transmit information regarding lead-related conditions to programmer 24 via telemetry module 88. For example, processor 80 may provide an alert regarding any detected lead-related conditions, or suggest a response to a lead-related condition. Alternatively, IMD 16 may provide the test results or other sensed signal to an external device, e.g., programmer 24, via telemetry module 88 for confirmation of identification of lead-related conditions. In some examples, processor 80 may provide the test results from numerous evaluation phases in the form of a trend diagram illustrating the values over time. Processor 80 may also receive information regarding lead-related conditions or responses to such conditions from programmer 24 via telemetry module 88 and/or receive user approval of a response.

In some examples, IMD 16 may communicate, via programmer 24 or another external device, with a network such as the Medtronic CareLink® Network developed by Medtronic, Inc., of Minneapolis, Minn., or some other network linking patient 14 to a clinician or other users. In such examples, IMD 16 may pass the alert through the network to such users.

If IMD 16 is configured to generate and deliver pacing pulses to heart 12, processor 80 may maintain programmable counters which control the basic time intervals associated with single or multiple chamber pacing. Generally, these intervals define when pacing, sensing, lead conductor integrity testing and other functionality are performed. Intervals defined by processor 80 may include atrial and ventricular pacing escape intervals, refractory periods during which sensed P-waves and R-waves are ineffective to restart timing of the escape intervals, and the pulse widths of the pacing pulses. The durations of these intervals may be determined by processor 80 in response to stored data in memory 82. Processor 80 may also determine the amplitude of the cardiac pacing pulses.

In examples disclosed herein, therefore, processor 80 identifies lead-related conditions during a test phase of the therapy delivery sequence/cycle by comparing one or more electrical characteristics/properties of the leads 18, 20, and 22 to one or more predetermined criteria. During the test phase, the electrodes 40, 42, 44, 46, 48, 50, 58, 62, or 66 associated with one or more leads 18, 20, 22 being tested are isolated from the lead(s), as discussed more fully with reference to FIGS. 6 and 7. In one example, one or more electrical properties of the lead(s) 18, 20, 22 are monitored and compared to respective predetermined criteria. In another example, a test signal may be delivered via an electrical path defined by a pair of conductors in one of leads 18, 20, and 22, and one or more electrical properties, such as impedance of the path, is measured and/or computed by processor 80 and compared to respective predetermined criteria stored in memory 82.

If the lead electrical properties traverse the predetermined criteria, a lead-related condition is identified. The disclosed lead-related condition identification techniques may, in general, be automatically triggered by processor 80 during the evaluation phase. The evaluation phase may be a predetermined period of time during a therapy delivery cycle such as the periods corresponding to an atrial blanking period (for an atrial lead) or a ventricular blanking period (for a ventricular lead) occurring between therapy delivery and sensing of intrinsic events.

In one example, sensing module 86 and/or processor 80 are capable of collecting, measuring, and/or calculating delivered energy and impedance data for any electrical path including two or more conductors. In such examples, sensing module 86 and/or processor 80 may collect, measure, and/or calculate energy and impedance data based on delivery of a test pulse between the conductors. Processor 80 may store detected delivered energy and impedance values in memory 82.

In some examples, IMD 16 detects and calculates electrical properties associated with the lead, such as delivered energy and impedance, respectively. Morphological and timing deviations as well as threshold crossings may also be calculated. For instance, a test signal in the form of a current pulse through first and second conductors may be delivered from stimulation generator 84, and the actual current delivered through the lead during delivery of the test signal measured. IMD 16, e.g., processor 80, calculates a resistance based upon the voltage amplitude of the pulse and the measured amplitude of the resulting current. In some examples, the leads 18, 20, and 22 include circuitry (FIGS. 6 and 7) for measuring amplitudes of resulting currents or voltages.

In certain cases, IMD 16 may calculate impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Additionally, delivered energy and impedance data may include actual, measured values, or may include values that can be used to calculate delivered energy and/or impedance, such as current and/or voltage values. For example, a delivered energy may include a measured current or voltage value rather than an energy value derived from a known voltage or current and a measured current or voltage. In some examples, a delivered energy may comprise a voltage or current measured during delivery of a constant voltage pulse or a voltage or current measured during delivery of a constant current pulse.

To identify lead-related conditions, processor 80 will compare the actual measured electrical characteristic(s) or properties of the conductor to pre-determined values. For example, at least one of either the delivered energy or the measured impedance to predetermined criteria. In some examples, processor 80 compares the actual energy delivered by the test signal or energy discharged through the conductors from an energy storage device to a pre-determined percentage value stored in memory 82.

Although signal generator 84, if functioning properly, will generate and deliver the programmed energy in the form of a voltage or current pulse to the electrical path defined by the test conductors, the energy actually delivered may be diminished in the event a lead-related condition exists somewhere along the electrical path through which the signal is delivered. In order to identify a lead-related condition, therefore, processor 80 may determine if the energy delivered during the test is less than a pre-determined percentage of the programmed energy of the signal. In some examples, the threshold percentage of programmed energy is in a range from approximately 60% to approximately 80%. In one example, the threshold percentage of programmed energy is approximately equal to 75%.

In the examples disclosed herein, processor 80 may perform lead integrity testing automatically during predetermined portions of a therapy delivery cycle. If an integrity issue is detected along one electrical path through which the signal is delivered, processor 80 may manipulate the conductor configurations to identify which conductor or connector of the path is experiencing an integrity issue. For example, if an integrity issue is detected in two of the conductors making up the path, it may be necessary to determine whether both or only one (and if so which) of the conductors is causing the issue.

Figure 5:
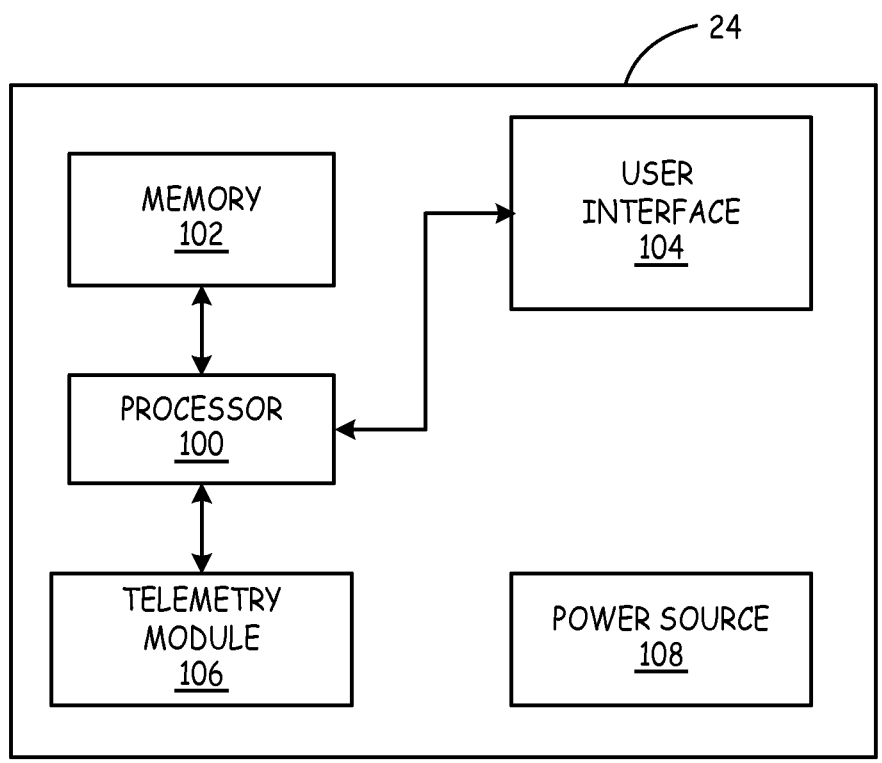
FIG. 5 is a functional block diagram illustrating an example configuration of an external programmer that facilitates user communication with the IMD.

The functions for identifying lead-related conditions attributed to processor 80 and memory 82 of IMD 16 may be implemented logically and/or physically as a separate module within IMD 16 or another device including, e.g., programmer 24. For example, IMD 16 may include a lead diagnostics unit having various modules for performing functions related to identifying lead-related conditions for any of leads 18, 20, 22. Each module of the lead diagnostics unit may be implemented in one or more processors, such as processor 80 of IMD 16, processor 100 of programmer 24 (FIG. 5). One or more modules of the lead diagnostics unit may additionally or alternatively be embodied in other digital or analog circuitry, such as diagnostic unit 700 (FIG. 7). The modules of the lead diagnostics unit may be embodied as one or more hardware modules, software modules, firmware modules, or any combination thereof. As described more fully with reference to FIGS. 6 and 7 herein, the lead diagnostics unit may automatically detect and analyze the energy delivered by and the lead impedance during the delivery of a test signal.

FIG. 5 is functional block diagram illustrating an example configuration of programmer 24. As shown in FIG. 5, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include a display to present graphical user interface to a user, and a keypad or another mechanism for receiving input from a user.

The user may also use programmer 24 to adjust or control the detection of lead-related conditions performed by IMD 16. For example, the user may use programmer 24 to program the thresholds to which delivered energy and lead impedance are compared, or any other aspects of the integrity test. In this manner, the user may be able to finely tune the integrity test to the specific condition of patient 14. In some examples, the user uses programmer 24 to control the performance of an integrity test for detecting lead-related conditions, e.g., in a clinic, hospital, or operating room setting, at the time of implant or during a follow-up visit.

In addition, the user may receive an alert from IMD 16 indicating a potential lead-related condition via programmer 24. The user may respond to IMD 16 by suggesting a response to a detected lead-related condition. Alternatively, IMD 16 may automatically suggest a response to a lead-related condition. Programmer 24 may prompt the user to confirm the response.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 100 of programmer 24 and/or one or more processors of one or more networked computers may perform all or a portion of the techniques described herein with respect to processor 80 and IMD 16. For example, IMD 16 may transmit parameters, such as delivered energy and impedance detected during delivery of a therapeutic electrical signal to patient 14 to programmer 24 via telemetry module 88. Processor 100 and memory 102 may store and process the electrical characteristics, such as delivered energy or impedance, in the manner described above with reference to processor 80 and memory 82 to identify lead-related conditions associated with one or more of leads 18, 20, 22 connected to IMD 16. In other examples, some of the functions associated with identifying lead-related conditions may be performed by IMD 16, while others are performed by programmer 24.

Figure 6:
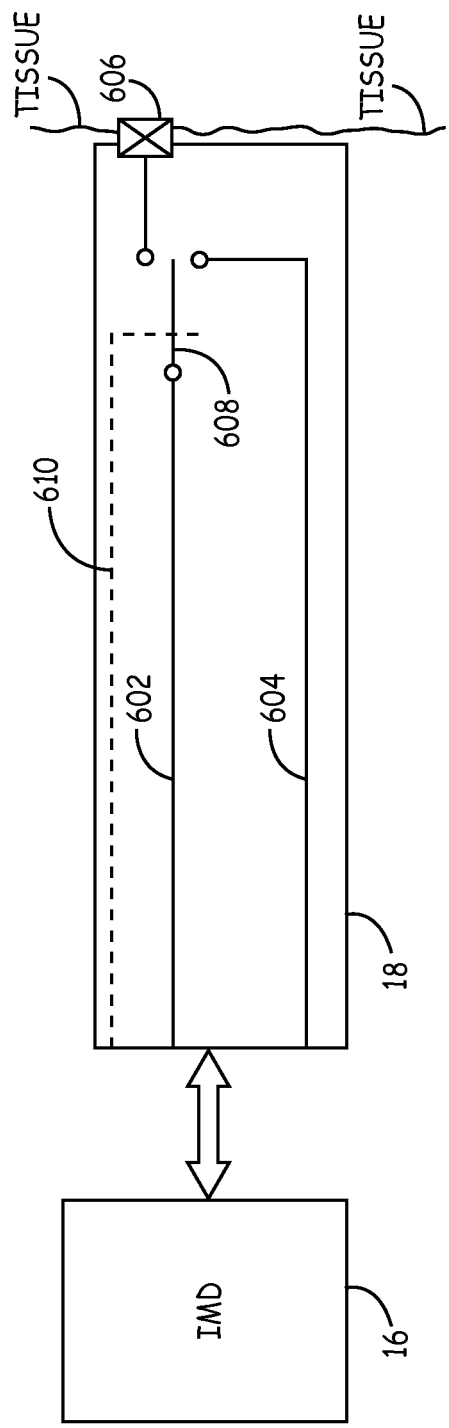
FIG. 6 illustrates an example embodiment of a schematic depicting conductive isolation of an implantable medical lead in accordance with principles of the disclosure.

FIG. 6 illustrates one embodiment of a schematic depicting conductive isolation of lead 18 in accordance with principles of the disclosure. The disclosure is not limited to lead 18 but rather is applicable to any of the other leads in the system. Lead 18 includes conductors 602, 604 that are typically electrically conductive for transmitting signals to and from the proximal and distal lead ends. In the illustrative embodiment, one of the conductors, 602 in this example, is selectively-coupled to an electrode or sensor element 606 that interfaces with tissue of the patient. However, in other embodiments such as FIG. 7, multiple conductors may be selectively-connected to tissue interfacing electrodes or sensor elements. Each of the conductors 602, 604 is typically electrically isolated from any other conductors in the system and encased within an outer sheath of the lead body for electrical insulation from body tissue and fluids. The conductors 602, 604 may both extend through the lead body from a connector assembly provided at a proximal lead end for connection with IMD 16 to the distal lead end or along a section of the lead body. The selective-coupling of the distal end of conductor 602 to electrode 606 is provided through actuation of a switching element 608.

Switching element 608 is employed to configure the conductors for either therapy delivery or for the conductor evaluation state. Switching element 608 may be any electrical component (implemented via hardware and/or software, e.g., a switch or a multiplexer) that will permit the toggling between ON and OFF states, where in an ON state, contact is provided between the conductor and the electrode or sensor element terminals. Control signals, as illustrated by the dotted line 610, may be issued by IMD 16 to enable toggling of the switching element between ON and OFF states. The minimal and temporary source of power required to perform the switching will be provided to switching element 608 by the IMD 16 power source.

Additionally, the switching element 608 may be utilized to couple the conductors 602, 604 together to establish a conductive path from and to the IMD 16, while isolating the path from the tissue. Therefore, the control signal 610 may be employed to provide the instructions to switch coupling of switching element 608 to either couple conductors 602, 604 to the electrode/sensor element during the pace/sense states or decouple the contact during the evaluation phase and couple conductors 602, 604 together. Thus, the processor 80 will effectively perform signal redirection. Active switching through the switching element 608 will provide a mechanism allowing the IMD 16 to schedule evaluations of the conductors 602, 604 and to direct a test signal through the two conductors only. In other words, the switching element 608 will disconnect the path to the tissue interfacing electrode or sensor elements 606 and couple the conductors 602, 604 directly or through a conductive element 610 to define a complete conductive path. In an exemplary implementation, the conductive element 610 may be a single conductive wire comprised of the same material constituting conductors 602, 604. As such a controlled path to and from the IMD 16 looping through the conductors 602, 604 will be provided with the path being conductively isolated from the cardiac tissue.

Conductive isolation is generally an electrical disconnection and isolation of conductors 602, 604 from cardiac tissue during a pre-determined period of time, the evaluation state, during which the lead integrity assessment of the present disclosure is performed. Unlike the conventional lead integrity assessments, isolating the cardiac tissue from the conductive path during the evaluation state eliminates the variability that arises from tissue-related impedance. Isolating the lead conductors removes the cardiac tissue from the circuit path and, therefore confines the measurement of electrical characteristics to the lead conductors. As such, the isolation eliminates tissue variations due to cardiac remodeling and disease related conditions while at the same time increasing the ability to monitor lead electrical characteristics with greater resolution and sensitivity.

The aforementioned lead diagnostics unit controls the configuration of the conductors for either therapy delivery or for the evaluation state. The diagnostic unit determines parameters for the conductor evaluation based on lead surveillance parameters and other algorithmic decisions that may be stored within memory of the IMD 16. The diagnostic unit may consist of one or more modules implemented as hardware and/or software instructions within IMD 16 or as a separate component within the lead (for example, as shown in FIG. 7). In the example of FIG. 6, it should be understood that the diagnostic unit is embodied as software within processor 80.

During the evaluation state, the diagnostic unit may in one embodiment control the stimulation generator to transmit test signals through the coupled conductors. The test signals are propagated through the conductors and received by the diagnostic unit for processing and evaluation of the lead conductor integrity. Based on the results of the evaluation, processor 80 will take appropriate action, as described below, if a lead-related condition is identified. The test signals may be targeted toward specific conditions and will elicit the behaviors associated with a certain class of lead-related condition. Examples of such conditions include behaviors associated with compromised lead-body insulation, intermittent conductor fractures and complete lead fractures.

The test signals may be characterized by duration of the signal, signal amplitudes, morphologies, and patterns and frequency. These signals may be digitized pulses or analog signals. For example, a test signal to test insulation-related conditions may comprise a sine wave at a frequency that is outside the frequency range of a physiological waveform. In another example, the test signal may be a pulse train of about 10 ms comprised of a pre-selected number of pulses with a pre-determined pulse width. The test signal may be issued in a repeatable sequence for evaluation by the diagnostic unit.

The test signals or pulses are evaluated against their original properties, including the number of pulses, durations, and other defining characteristics. The test signals may be received by a signature generator or a linear feedback shift register (LFSR) that compresses the received signal while maintaining all the information in preparation for evaluation. An evaluation signature is then generated by the signature generator or the LFSR based on the received test signal. The generated signature is then compared to a predetermined comparison signature with the result of the comparison indicating whether the conductive path is interrupted.

The comparison signature used for the comparison test may be based on a pre-implant or shortly-after-implant evaluation of the conductors and may be stored in memory or a register. If the evaluation signature does not match the comparison signature, notification to the patient of a lead-related condition may be initiated. In alternative embodiments, the diagnostic unit may re-execute the comparison test via alternative conductive paths whereby a different conductor (not shown) is coupled to each of the two previously tested conductors 602, 604. In doing so, a single-path lead-related condition will produce a different signature compared to the signature obtained in the initial fault isolated to the conductive path exhibiting a diverging signature. The diagnostic unit may remedy the lead-related condition by electrically disconnecting the faulty conductor from the circuits and/or electrode and then reconfiguring the functional path to a secondary path that has been previously deemed to function appropriately. The secondary path may be on a conductor within the same lead or a conductor in a different lead.

In alternative embodiments, one or more electrical properties of the conductors 602, 604 may be measured during the evaluation state. For example, the test signal may be employed to measure the impedance of the conductors 602, 604 based on output current and voltage amplitudes. The conductive isolation will provide a far more sensitive and precise impedance measurement of the conductors 602, 604 because the tissue will be isolated from the conductors during the evaluation.

Figure 7:
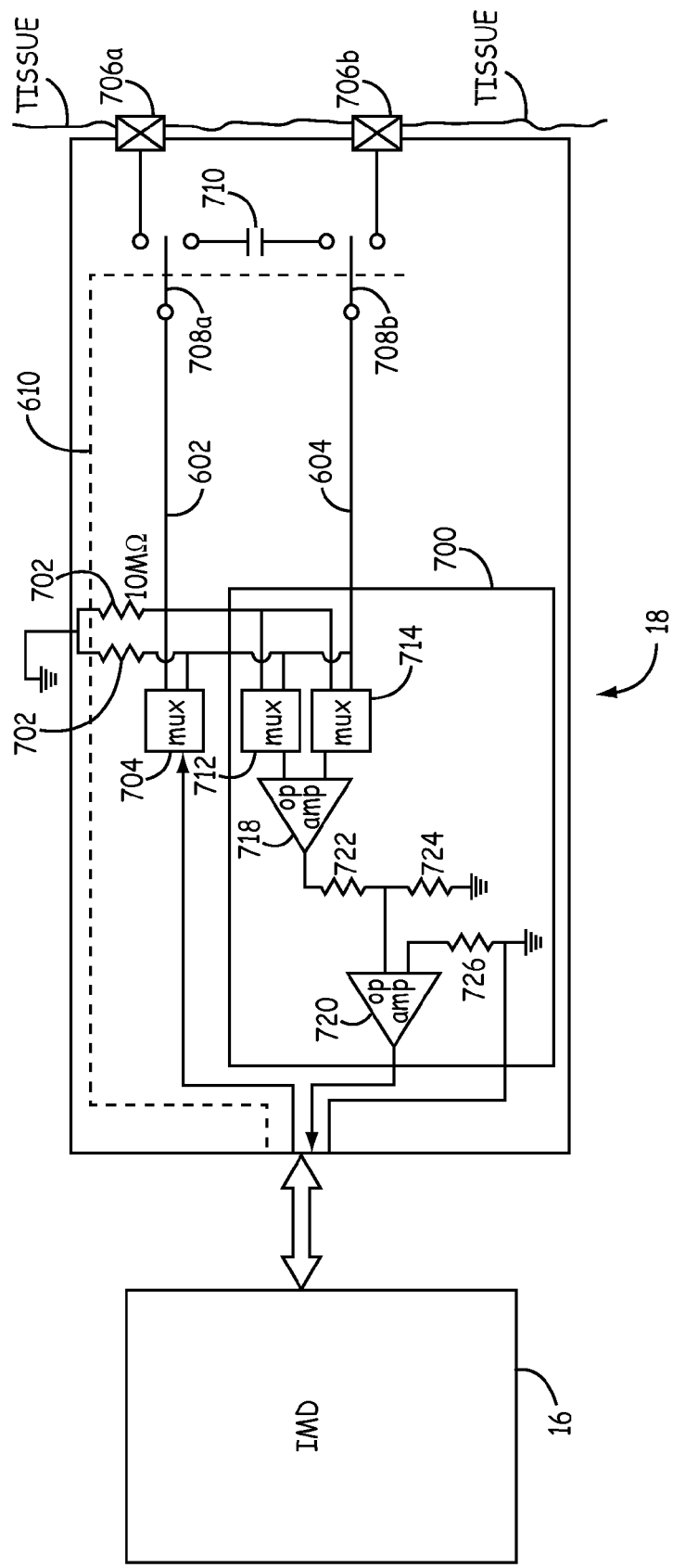
FIG. 7 illustrates another example embodiment of a schematic depicting conductive isolation of an implantable medical lead in accordance with principles of the disclosure.

FIG. 7 illustrates another embodiment of a schematic depicting conductive isolation of an implantable medical lead coupled to an implantable medical device in accordance with principles of the disclosure. The illustrative embodiment shows IMD 16 coupled to lead 18 which includes a diagnostic unit 700. Conductors 602, 604 are disposed within the body of lead 18 and connected to a pair of tissue interfacing electrode or sensor elements 706a, 706b. The connection between conductors 602, 604 to elements 706a, 706b is made by a pair of switching elements 708a, 708b controlled via a control signal 610 as previously described.

The switching elements 708a, 708b are alternatively employed to provide a conductive path that isolates conductors 602, 604 from electrode or sensor elements 706a, 706b. To that end, a capacitor 710 is disposed within the lead body and the terminals of the capacitor 710 are coupled to the switching elements 708a, 708b to redirect the electrical path between the conductors 602, 604 through the capacitor. Although the illustration shows the capacitor 710 disposed on the distal lead end, it should be understood that the capacitor may be disposed at any suitable location on the lead body. The capacitor 710 may be utilized in conjunction with diagnostic unit 700 during the evaluation phase to assess the integrity of conductors 602, 604.

In one embodiment, the diagnostic unit 700 includes functionality for energy detection, threshold comparison, and integrity indication. The circuitry for performing the energy detection may comprise multiplexers (mux) 712, 714, with each multiplexer being coupled to both conductors 602, 604, and op amp 718. The energy detection circuitry detects the energy discharged from capacitor 710 during the evaluation state. In the example, the terminals of op amp 718 are coupled to both conductors 602, 604 via the outputs of mux 712, 714. It should be noted that the terminals of mux 712, 714 are configured so that each conductor 602, 604 is coupled to one or the other mux at a time. The threshold comparison function is performed by op amp 720. Specifically, the output signal of op amp 718 is voltage divided by the dual resistors 722, 724 with the resulting signal being coupled to a first terminal of op amp 720. The second input terminal of op amp 720 receives a programmable threshold voltage via resistor 726 so that the output of op amp 720 corresponds to either the voltage from the capacitor 710 or the programmable threshold voltage.

The integrity indication functionality is embodied in a timer (not shown) and instructions in processor 80 that determine the time that elapses prior to the threshold voltage crossing. If the elapsed time interval does not fall within a predetermined confirmation interval, the processor 80 may determine that a lead-related condition is present. Measurement of the rate of discharge of capacitor 710 may also be performed through conventional methods such as that described in U.S. Pat. No. 5,137,021, issued to Wayne et al., which is incorporated herein by reference in its entirety.

It should be noted that the implementation of the present disclosure is not limited to a lead having two conductors. Rather, alternative embodiments can be implemented with any number of conductors, including one or more than two, without departing from the scope of the disclosure. Nor do the conductors all have to be coupled to an electrode as was described in conjunction with FIG. 6.

Figure 8:
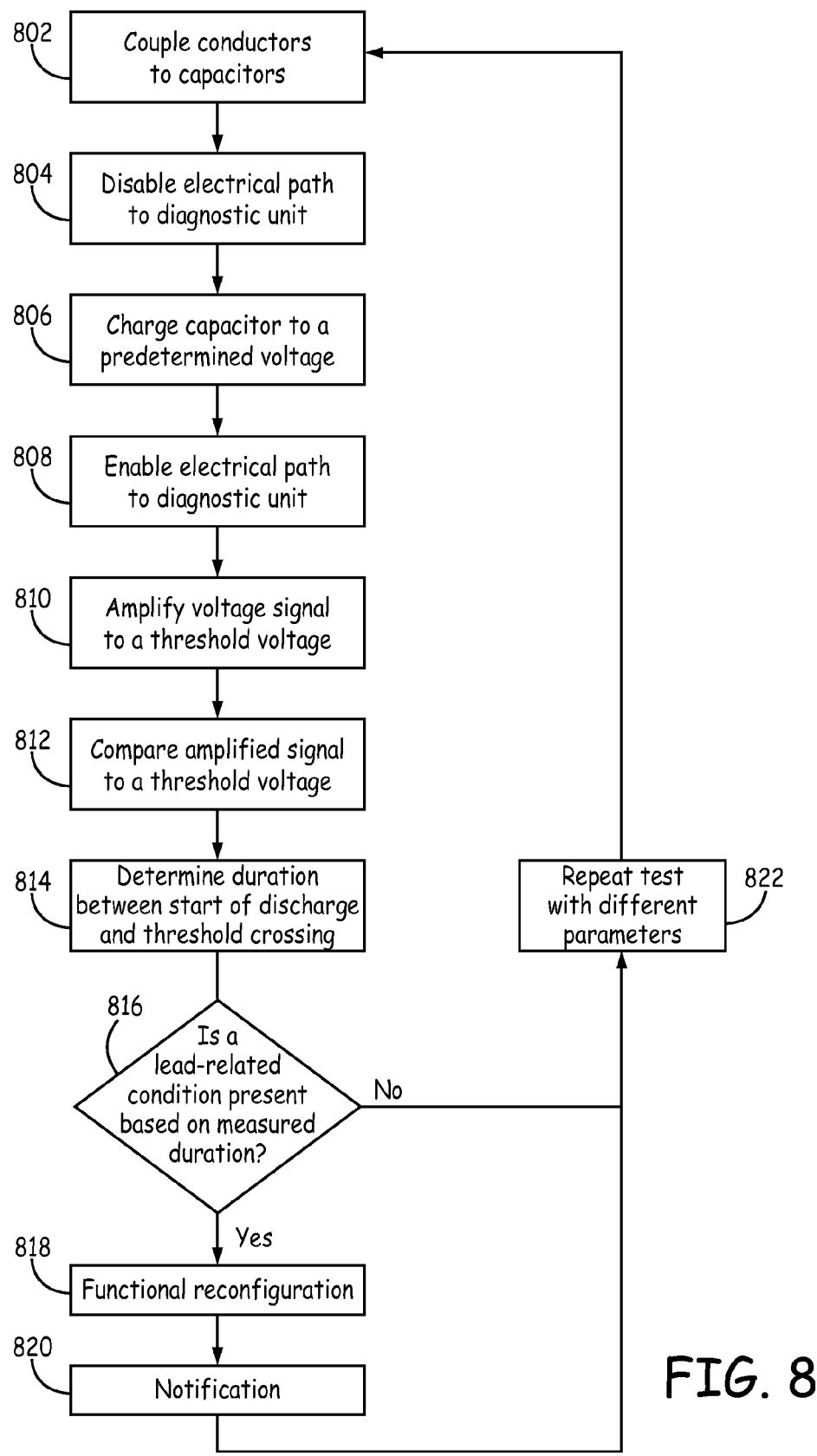
FIG. 8 is a flow chart illustrating exemplary operational aspects of the evaluation phase.

FIG. 8 is a flow chart illustrating exemplary operational aspects of the evaluation phase. In the illustrative embodiment, the capacitor 710 is charged and discharged through the isolated conductors 602, 604. The diagnostic unit 700 subsequently evaluates the discharge morphology of the capacitor to assess the integrity of the conductors. In particular, the evaluation phase is initiated (block 802) by coupling conductors 602, 604 directly to capacitor 710 via switching element 708a, 708b. Mux 704 is also selected to couple conductors 602, 604 to the power source in IMD 16 and (block 806) the capacitor 710 is charged to a predetermined voltage of, for example, 3 volts. During the charging of capacitor 710, mux 712, 714 may be disabled (block 804). After capacitor 710 is charged, mux 704 may be disabled and the discharge path established (block 808) through mux 712, 714. Op amp 718 is configured as a differential amplifier which receives and amplifies (block 810) a signal representing the capacitor 710 discharge voltage and provides an output of the amplified signal. The amplified signal is voltage divided and coupled to one input terminal of op amp 720, which is configured as a comparator. The amplified signal representing the discharge morphology of capacitor 710 is compared (block 812) to a programmable threshold voltage as the confirmation capacitor discharges.

A timer may be synchronized with the start of the discharge of capacitor 710 and to compute (block 814) the duration between the start of discharge until the time when the output of op amp 720 is tripped due to the differential output crossing the programmed threshold voltage. The duration measured will indicate the time for the confirmation capacitor to discharge to a programmed threshold voltage such as 0.25V from the exemplary starting voltage of 3.0V, for example. In that example, a duration differing from a pre-determined duration will trigger a determination of existence of a lead-related condition whereas a duration matching the pre-determined duration will indicate conductive integrity.

The measured duration is evaluated to determine whether a lead-related condition is present (block 816). In one example, the test results of the evaluation phase may be transmitted to processor 80 for interpretation to determine whether a lead-related condition is present. Processor 80 may take one or more actions in response to detecting a lead-related condition. For example, processor 80 may reconfigure (block 818) sensing and/or therapy delivery to avoid use of a conductor identified as having a lead-related condition. Additionally or alternatively, processor 80 may reconfigure sensing and/or therapy delivery parameters for a conductor having a lead-related condition. As one example, processor 80 may select different combinations of electrodes to deliver therapy to patient 14. As another example, processor 80 may extend the blanking period of one or more sensing channels, e.g., amplifiers, of sensing module 86. In one more example, processor 80 may increase a sensing threshold, e.g., a threshold used to detect cardiac events, such as depolarizations, following delivery of a therapeutic electrical signal, e.g., an antitachycardia pacing pulse. Extending a blanking period and/or increasing a threshold value may help prevent inappropriate detection of arrhythmias and/or other cardiac events.

Functional reconfiguration on detection of a system fault may be achieved automatically or by reprogramming. The option to reprogram functionality and to reconfigure provides an alternative to lead extraction while maintaining pacing and sensing functionality even after impairment of a particular conductor pathway. Automatic reprogramming and reconfiguration ensures that therapy will continue to be delivered to the patient even after a non-catastrophic subsystem impairment to a lead component.

A notification (block 820) may also be communicated to alert the patient and/or clinician of the determination of that a lead-related condition has been detected.

If a lead-related condition is suspected, but not confirmed, based on the results of a given evaluation phase, the assessment may be repeated (block 822) with different programmable thresholds to determine whether a lead-related condition is present.

Alternatively, if a lead-related condition is confirmed based on the results of a given evaluation phase, the evaluation phase may be repeated (block 822) with different programmable thresholds to further characterize the nature of the condition. The conductor assessment may be repeated with each of the mux 704, 712, 714 swapping the coupling selection of conductors 602, 604 to the previously deselected conductor. Alternating the selection will enable the diagnostic unit to pinpoint the conductor with the lead-related condition by comparing results for both conductors. If conductor 602 is fractured, for example, then the capacitor 710 will not charge properly. On discharge, the starting voltage will be at 0 volts. If conductor 602 is intermittent, capacitor 710 may charge partially and the test duration on discharge will reflect that state. Alternating the selection by the mux 704, 712, 714 will similarly identify a condition associated with conductor 604.

Although detection of lead-related conditions is directed herein toward a cardiac device, this disclosure may also be applicable to any medical device, e.g., implantable or external, that includes leads to sense and/or deliver electrical signals in which detection of lead-related conditions may be appropriate. These devices include those for providing spinal cord stimulation, deep brain stimulation, pelvic floor stimulation, gastric stimulation, occipital stimulation, functional electrical stimulation, and any other stimulation therapy utilizing electrode sensing and/or stimulation methods. Furthermore, although described herein as implemented by an IMD and system including an IMD, in other examples, the techniques described herein may be implemented in an external pulse generator. An external pulse generator may be coupled to leads during implant or during a device changeout to perform a lead integrity test as described herein to detect any lead-related conditions of implanted leads.

The techniques described in this disclosure, including those attributed to the implantable leads, IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated, analog, or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples for detecting lead-related conditions have been described. These and other examples are within the scope of the disclosure defined by the following claims.

What is claimed is:

1. A medical electrical lead-electrode system, comprising:
   a stimulus therapy generator;
   an electrode for interfacing with tissue of a patient;
   a first conductor having a first distal end connected to the tissue interface electrode and a first proximal end connected to the stimulus therapy generator;
   a second conductor having a second proximal end connected to the stimulus therapy generator;
   means for isolating the first distal end of said first conductor from the tissue interface electrode and for coupling said first distal end to the second distal end of said second conductor, wherein the stimulus therapy generator generates a signal for transmission through the first and second conductor; and
   a signal processor for receiving the signal propagated through the first and second conductors.

2. The medical electrical lead-electrode system of claim 1, further comprising control means for controlling the isolating and coupling means.

3. The medical electrical lead-electrode system of claim 1, wherein the isolating means disconnects the tissue interface electrode from the first conductor to directly connect the first distal end to the second distal end.

4. The medical electrical lead-electrode system of claim 3, wherein the isolating means disconnects the tissue interface electrode from the first conductor in response to generation of the test signal.

5. The medical electrical lead-electrode system of claim 4, wherein the test signal is generated at a predetermined period following issuance of a pacing pulse.

6. The medical electrical lead-electrode system of claim 4, wherein the test signal is generated during a blanking period following a ventricular event.

7. The medical electrical lead-electrode system of claim 4, wherein the test signal is generated during a blanking period following an atrial event.

8. The medical electrical lead-electrode system of claim 1, wherein the signal processor includes:
   a differential amplifier configured to receive a signal from the first conductor and the second conductor; and
   a comparator configured to compare the output of the differential amplifier with a programmable threshold voltage.

9. The medical electrical lead-electrode system of claim 1, wherein the isolating means comprises a switch.

10. The medical electrical lead-electrode system of claim 1, wherein the isolating means comprises a multiplexer.

11. A method of detecting a fault in a medical electrical lead, comprising:
    providing a first conductor and a second conductor;

providing a first electrode;

providing a first switch;

selectively actuating the first switch to couple the first electrode to a first distal end of the first conductor; and providing a controller communicatively coupled to the first switch for transmitting a control signal, wherein in response to receiving the control signal, the first switch decouples the first electrode from the first conductor and directly couples the first conductor to the second conductor.

12. The method of claim 11, further comprising providing a diagnostic unit configured to receive and process a signal from the first and second conductor to detect a fault in the first and second conductors.

13. The method of claim 11, wherein the controller is configured to transmit the control signal during a blanking period of a cardiac therapy delivery cycle.

14. The method of claim 11, wherein the controller is configured to transmit the control signal at a predetermined period following issuance of a pacing pulse.

15. The method of claim 11, further comprising:

providing a second electrode;

providing a second switch communicatively coupled to the controller; and selectively actuating the second switch to couple the second electrode to a second distal end of the second conductor, wherein in response to receiving the control signal, the second switch decouples the first electrode from the second conductor.

* * * * *